United States Patent [19]

Bigg et al.

[11] Patent Number: 4,559,356

[45] Date of Patent: Dec. 17, 1985

[54] 2-(INDEN-2-YL)-IMIDAZOLINE DERIVATIVES, PROCESS FOR THEIR PREPARATION AND PHARMACEUTICAL COMPOSITIONS CONTAINING THEM

[75] Inventors: Dennis Bigg; Jacques Menin, both of Paris, France

[73] Assignee: Synthelabo, Paris, France

[21] Appl. No.: 590,355

[22] Filed: Mar. 16, 1984

[30] Foreign Application Priority Data

Mar. 18, 1983 [FR] France .................. 83 04524

[51] Int. Cl.[4] .................. A01K 31/415; C07D 233/06; C07D 233/22
[52] U.S. Cl. ...................................... 514/401; 548/347
[58] Field of Search ...................... 548/347; 424/273 R; 514/401

[56] References Cited

U.S. PATENT DOCUMENTS 2,731,471  1/1956  Synerholm et al. ............ 548/347 X
2,842,478  7/1958  Gardocki et al. ............... 548/347 X
3,287,469  11/1966  Harvey, Jr. et al. ............... 548/347

Primary Examiner—Joseph Paul Brust
Attorney, Agent, or Firm—Wegner & Bretschneider

[57] ABSTRACT

Compounds of the general formula (I)

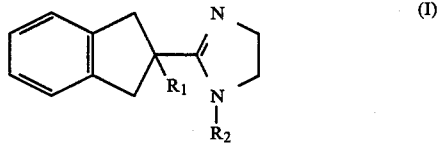

in which $R_1$ is a hydrogen atom or a $(C_1-C_4)$-alkyl, benzyl, phenethyl or methoxy group and $R_2$ is a hydrogen atom or a methyl group, and their addition salts with pharmaceutically acceptable acids are useful, as such or in pharmaceutical compositions containing them in association with excipients, as $\alpha_2$-antagonists.

3 Claims, No Drawings

2-(INDEN-2-YL)-IMIDAZOLINE DERIVATIVES, PROCESS FOR THEIR PREPARATION AND PHARMACEUTICAL COMPOSITIONS CONTAINING THEM

The present invention relates to 2-(inden-2-yl)-imidazoline derivatives which, in the form of the free base, are of the general formula (I)

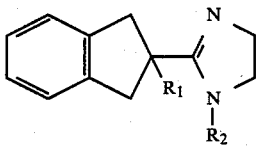

in which $R_1$ is a hydrogen atom or a $(C_1-C_4)$-alkyl, benzyl, phenethyl or methoxy group and $R_2$ is a hydrogen atom or a methyl group.

These compounds may also exist in the form of addition salts with acids, in particular pharmaceutically acceptable acids.

The preferred compound according to the invention is that of formula (I) in which $R_1$ and $R_2$ each represent a hydrogen atom.

The compounds of formula (I) can be prepared by known methods, starting from a 2,3-dihydro-1H-indene-2-carboxylic acid ester of the formula (II),

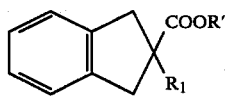

in which $R_1$ is as herein defined and $R'$ is, for example, a methyl or ethyl group, by reaction with a diamine of the formula $R_2NHCH_2CH_2NH_2$ in which $R_2$ is as herein defined, in the presence of trimethyl-aluminium. If desired the compound of formula (I) can be converted into an acid addition salt in manner known per se.

The starting ester of formula (II) in which $R_1$ is a hydrogen can be prepared, for example, in accordance with the method of Perkin and Revay, described in J. Chem. Soc., 65, 228 (1894).

In order to obtain esters of formula (II) in which $R_1$ is an alkyl, benzyl or phenethyl group, alkylation is carried out beforehand with a compound of the formula $R_1X$, in which X is a nucleofugic group such as an iodine or bromine atom, after the anion has been formed by means of a base, such as lithium diisopropylamide (LDA), in accordance with the following equation

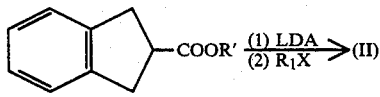

Finally, in order to obtain esters of formula (II) in which $R_1$ is a methoxy group, it is possible to use 2-hydroxy-2,3-dihydro-1H-indene-2-carboxylic acid as starting material, to esterify this acid in a known manner with an alcohol R'OH and to methylate the ester by means of iodomethane in the presence of sodium hydride in a solvent, such as dimethylformamide, in accordance with the following equation

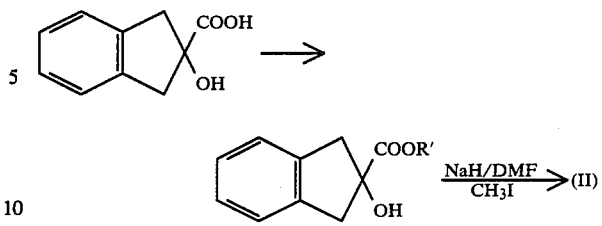

The above acid starting material can be prepared in accordance with the method described in C.R. Acad. Sc. Paris, 263 325-9 (1966).

The following Examples give a more detailed illustration of the preparation of compounds according to the invention. The IR and NMR spectra confirm the structures of the compounds obtained.

EXAMPLE 1

2-(2,3-Dihydro-1H-inden-2-yl)-4,5-dihydro-1H-imidazole 26 ml (0.0624 mol) of 25% strength trimethylaluminium in hexane, and 50 ml of toluene are introduced into a three-necked flask, under argon. A solution of 3.8 g (0.0637 mol) of ethylenediamine in 20 ml of toluene is added dropwise at a temperature between 0° and 5° C. The reaction mixture is allowed to return to room temperature and is heated to 50° C. 7.05 g (0.04 mol) of methyl 2,3-dihydro-1H-indene-2-carboxylate are added dropwise at this temperature.

The hexane is distilled off and the mixture is heated at the reflux temperature of toluene for 45 minutes.

The mixture is hydrolysed with 60 ml of water, with cooling, 100 ml of ethyl acetate are added, the inorganic product is filtered off and the organic phase is washed with water, dried over magnesium sulphate and evaporated.

A solid is collected, and is triturated in petroleum ether. Melting point: 122°-123° C.

The fumarate is prepared in isopropyl alcohol by mixing 6.4 g (0.0343 mol) of base and 3.7 g (0.0316 mol) of fumaric acid. The mixture is evaporated to dryness and the fumarate is recrystallised from ethanol. Melting point: 202°-203° C.

EXAMPLE 2

2-(2-Propyl-2,3-dihydro-1H-inden-2-yl)-4,5-dihydro-1H-imidazole (a) 30 ml (0.048 mol) of a 1.6M solution of butyllithium in hexane are introduced into a solution of 6.7 ml (0.048 mol) of diisopropylamine in 50 ml of tetrahydrofuran at −78° C., under argon.

The mixture is stirred at −78° C. for 1 hour and 7.05 g (0.040 mol) of methyl 2,3-dihydro-1H-indene-2-carboxylate, dissolved in 30 ml of tetrahydrofuran, are introduced. Stirring is continued at −78° C. for 1 hour and 34 g, that is to say 19.5 ml (0.2 mol), of iodopropane are added. The mixture is stirred at −78° C. for 1 hour and is allowed to return to room temperature, stirring is continued for 1 hour and the mixture is poured onto ice-water and extracted with ether and the extract is washed with water, dried over magnesium sulphate and evaporated. An oil remains, and is distilled at 160°-170° C. under about 2,600 Pa (20 mm Hg) and purified by passage over a silica column, the column being eluted with a 60/40 mixture of methylene chloride and petroleum ether.

(b) 19.7 ml, that is to say 3.38 g (0.047 mol), of trimethyl-aluminium (25% strength in hexane), dissolved in 50 ml of toluene, are introduced into a flask, and 3.3 ml, that is to say 2.87 g (0.048 mol), of ethylenediamine, dissolved in 20 ml of toluene, are added dropwise at between 0° and 5° C., under argon.

The mixture is heated to 50° C. and 6.55 g (0.030 mol) of the oil obtained above, dissolved in 20 ml of toluene, are added dropwise.

The mixture is heated to distil off the hexane, and is brought to the reflux temperature of toluene for 45 minutes.

The mixture is cooled and 45 ml of water are added dropwise. Ethyl acetate is added, the solid is filtered off and the organic phase is separated off, washed with water, dried over magnesium sulphate and evaporated.

The residue, when triturated in petroleum ether, filtered off and dried, has a melting point of 141°–142° C.

The fumarate is prepared in a solution of fumaric acid in isopropyl alcohol, and the salt precipitated is recrystallised from ethanol. Melting point: 186°–187° C.

EXAMPLE 3

2-(2,3-Dihydro-1H-inden-2-yl)-1-methyl-4,5-dihydro-1H-imidazole 16.4 ml, that is to say 2.81 g (0.039 mol) of trimethylaluminium (25% strength in hexane), dissolved in 50 ml of toluene, are introduced into a flask and 3.51 ml, that is to say 2.95 g (0.040 mol) of N-methylethylenediamine, dissolved in 50 ml of toluene, are introduced dropwise at between 0° and 5° C., under argon.

The mixture is heated to 50° C. and 4.4 g (0.025 mol) of methyl 2,3-dihydro-1H-indene-2-carboxylate are added dropwise.

The mixture is heated in order to distil off the hexane and is brought to the reflux temperature of toluene for 45 minutes. It is allowed to cool and 37.5 ml of water are added dropwise.

The preparation is ended as in the above example, and the fumarate is collected. Melting point: 171°–172° C.

EXAMPLE 4

2-(2-Methoxy-2,3-dihydro-1H-inden-2-yl)-4,5-dihydro-1H-imidazole (a) 40.5 g (0.227 mol) of 2-hydroxy-2,3-dihydro-1H-indene-2-carboxylic acid are esterified in the presence of 32.5 g (0.273 mol) of thionyl chloride, dissolved in an excess of ethanol, at the reflux temperature for 8 hours. The ethyl ester obtained has a melting point of 90°–91° C.

(b) 2.1 g (0.044 mol) of 50% strength sodium hydride which has first been washed with pentane are introduced into a conical flask, under argon, together with 50 ml of tetrahydrofuran and 5 ml of dimethylformamide.

8.25 g (0.04 mol) of the hydroxylated ester prepared above are added dropwise, which causes evolution of hydrogen.

After the mixture has been stirred at room temperature for one hour, 12.5 ml, that is to say 28.4 g (0.2 mol), of iodomethane are added and the mixture is stirred at room temperature for a further 4 hours.

The mixture is then poured into water acidified with hydrochloric acid and is extracted with methylene chloride, and the extract is washed with water, dried and evaporated. An oil results, and is purified by passage over silica, the silica being eluted with methylene chloride.

(c) 40 ml of toluene and 20.7 ml (0.0495 mol) of trimethyl-aluminium, in 1.6M solution in hexane, are introduced into a reactor.

3.04 g (0.0506 mol) of ethylenediamine, dissolved in 20 ml of toluene, are added dropwise, whilst maintaining the temperature at between 0° and 5° C.

The mixture is allowed to come to room temperature and is heated to 50° C., and 7 g (0.0317 mol) of the oil obtained above, dissolved in 30 ml of tetrahydrofuran, are added dropwise.

The mixture is heated to distil off the hexane and is brought to the reflux temperature of toluene for 45 minutes.

The mixture is allowed to cool and is hydrolysed with 45 ml of water, and ethyl acetate is added.

The organic phase is isolated, washed, dried and evaporated.

The residue is taken up and its fumarate is prepared in isopropyl alcohol. Melting point: 129°–130° C.

The following table illustrates the structures and physical properties of various compounds according to the invention.

TABLE

| Compound | $R_1$ | $R_2$ | Melting point (°C., fumarate) |
|---|---|---|---|
| 1 | H | H | 202–203 |
| 2 | —CH$_2$CH$_3$ | H | 182–183 |
| 3 | —CH$_2$CH$_2$CH$_3$ | H | 186–187 |
| 4 | —CH$_2$CH$_2$CH$_2$CH$_3$ | H | 178–179 |
| 5 | —CH$_2$C$_6$H$_5$ | H | 158–159 |
| 6 | —CH$_2$CH$_2$C$_6$H$_5$ | H | 180–181 |
| 7 | H | CH$_3$ | 171–172 |
| 8 | —OCH$_3$ | H | 129–130 |

The compounds according to the invention were subjected to pharmacological tests which demonstrated their usefulness as $\alpha_2$-antagonists.

For this purpose, the compounds were studied in the test for potentiality and selectivity of antagonists with respect to $\alpha_2$-receptors in vitro.

The pA$_2$ value in respect of the inhibitory effects of clonidine, a well-known $\alpha_2$-agonist, was determined on the vas deferens in rats stimulated at a frequency of 0.1 Hz in the presence of 30 nmol of prazosin and 1 μmol of cocaine, in accordance with the method described by G. M. Drew (European Journal of Pharmacology, 42, (1977) 123–130).

The pA$_2$ values of the compounds according to the invention range from 6.0 to 8.3.

Their acute toxicities have also been studied on mice, using the intraperitoneal route. The lethal doses LD$_{50}$ range from 10 to 60 mg/kg.

The compounds according to the invention can be used for the treatment of depression (either by themselves or in combination with a product which inhibits the neuronal captation mechanisms), the treatment of hypotension and the treatment of post-operative paralytic ileum.

According to the invention, the pharmaceutical compositions can be in a form suitable for oral, rectal or parenteral administration; for example in the form of capsules, tablets, pellets, liquid capsules or solutes, or drinkable syrups or suspensions, and can contain suitable excipients.

The daily posology can range from 1 to 30 mg/kg, administered orally.

We claim:

1. Compounds of the general formula (I)

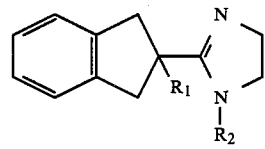

in which $R_1$ is a hydrogen atom or a $(C_1-C_4)$-alkyl, benzyl, phenethyl or methoxy group and $R_2$ is a hydrogen atom or a methyl group, and their pharmaceutically acceptable acid addition salts.

2. Compound according to claim 1, wherein $R_1$ and $R_2$ each represent a hydrogen atom and its pharmaceutically acceptable acid addition salts.

3. A pharmaceutical composition for use as an $\alpha_2$-antagonist which comprises, as active ingredient, an $\alpha_2$-antagonistically effective amount of a compound or salt as claimed in claim 1 in association with a suitable excipient.

* * * * *